United States Patent [19]
Chodorow

[11] Patent Number: 6,065,479
[45] Date of Patent: May 23, 2000

[54] DENTAL FLOSSER WITH BENDABLE SIDE WINGS

[75] Inventor: Ingram S. Chodorow, Carlsbad, Calif.

[73] Assignee: Placontrol, Inc., Rancho Santa Fe, Calif.

[21] Appl. No.: 09/175,184

[22] Filed: Oct. 20, 1998

[51] Int. Cl.[7] .................................................. A61C 15/04
[52] U.S. Cl. ............................................................ 132/323
[58] Field of Search .................................... 132/323, 327, 132/324, 325, 326; 433/141; D28/66, 67, 68

[56] References Cited

U.S. PATENT DOCUMENTS

| | | | |
|---|---|---|---|
| D. 251,075 | 2/1979 | Schiff | D28/68 |
| 4,736,757 | 4/1988 | Badoux | 132/323 |
| 4,982,752 | 1/1991 | Rodriguez | 132/327 |
| 5,388,600 | 2/1995 | Hart | 132/323 |
| 5,692,531 | 12/1997 | Chodorow | 132/323 |

Primary Examiner—Nicholas D. Lucchesi
Attorney, Agent, or Firm—Ostrolenk, Faber, Gerb & Soffen, LLP

[57] ABSTRACT

A dental flosser having a pair of spaced apart arms across which a strand of dental floss is extended and a handle extending in a direction different from said the arms, the arms and handle being essentially a flat contiguous injection molded plastic board, the handle having an aperture through its central area bordered by a pair of legs which are bendable to converge toward each other, a pair of wings extending from both outside edges of these legs, each wing being bendable out of the plane of the board to extend transversely therefrom to provide a surface thicker than the original edge of the handle, each of the arms being an extension of one of the legs so that when the legs are pressed toward each other the corresponding arms are urged to diverge from each other, thus stretching and tensioning the strand of floss extending therebetween with the wings providing a comfortable surface against which the users' fingers are pressed.

23 Claims, 7 Drawing Sheets

DENTAL FLOSSER WITH BENDABLE SIDE WINGS

RELATED INVENTIONS

This invention is related to disclosures in the following U.S. patents:

| U.S. Pat. No. | Inventor | Date |
|---|---|---|
| 4,006,750 | I. S. Chodorow | 02/08/77 |
| 4,016,892 | I. S. Chodorow | 02/08/77 |
| D 244,376 | I. S. Chodorow | 05/ /77 |
| D 250,214 | I. S. Chodorow | 11/07/78 |
| D 301,071 | R. Franchi | 05/09/89 |
| 5,086,792 | I. S. Chodorow | 02/11/92 |
| 5,538,023 | I. S. Chodorow | 07/23/96 |

BACKGROUND OF THE INVENTION

1. Field of the Invention

This invention is in the field of disposable dental flossing devices and particularly injection molded devices, each formed integrally as a handle plus a bow across which at least one strand of dental floss is spanned and may be manually tensioned by the user and in the field of manufacturing and packaging such dental flossing devices.

2. Background and Prior Art

This invention is in the field of devices for personal and professional dental care, particularly for removing plaque from the teeth surfaces and food particles from between teeth.

For many years teeth have been cleaned primarily by manual or power-driven brushes, and the spaces between teeth have been cleaned by a variety of methods including brushing, machine-driven jets of water, toothpicks, and the like and by flossing with the commonly available nylon dental floss and dental tape or thread or even rubber bands.

Until recently the most generally accepted objective in cleaning teeth was to remove food particles and chemicals, particularly sweets from tooth surfaces. However, now it has been established and is being taught by a growing number of dentists, orthodontists and periodontists, that the chief cause of caries (dental cavities) and a principal cause of periodontal (gum and root) disease is a bacterial plaque formation that develops on tooth surfaces. When removed, new plaque can reform in less than 24 hours. The causes of plaque development are not fully appreciated; however, a person's normal body chemistry independent of his or her particular diet can be a contributing factor.

Plaque is the name given to a bacterial substance that begins as an invisible film of micro-organisms and with saliva and foods, particularly sugars, forms a soft sticky white film on the surfaces of teeth and between teeth. If plaque is not removed daily it can develop and harden into a firmly attached substance called calculus or tartar which may cause gums to redden and swell in a condition known as gingivitis. This disease is often characterized by receding gums which causes the creation of small pockets around the teeth which trap food particles and bacteria. These pockets can enlarge if the gums become further inflamed or infected causing the bone supporting the teeth to become infected and destroyed. The weakened tissue is infection-prone and once so injured the gums cannot protect the underlying bone from the spread of this disease. Additionally, bacterial plaque produces noxious chemicals which cause cavities and irritate the gums. This is the manner in which teeth become loosened and ultimately lost, the latter stages here-described being periodontal disease.

Of the methods mentioned above for cleaning teeth, brushing is not effective to remove plaque from interdental tooth surfaces between the teeth. Water jets are not sufficiently abrasive to achieve plaque removal, though they may remove food particles very well. Also, toothpicks are too thick and cumbersome to probe and scrape between two closely adjacent surfaces. This leaves only dental floss, typically a strand of multifilamented nylon that is moved in a reciprocating action into the crack or space between the sides of two adjacent teeth. The unwaxed version of dental floss is less smooth and thus more abrasive and more effective in scraping plaque off the tooth enamel surfaces in question. However, the user of any floss has the problem of maneuvering the floss while it is under tension down between each pair of teeth. Positioning the floss is inconvenient in most teeth locations, quite difficult in many, and almost impossible in others. The procedure generally requires winding opposite ends of a strand around the middle finger of each hand respectively, then over the two index fingers of both hands which are placed into the mouth, attempting to position the span of floss between the fingers in the desired location, and finally reciprocating the floss between teeth while also moving it vertically along the tooth from tip to gum. The floss is maneuvered preferably just under the edge of the gum, held firmly against and wrapped partially around the proximal surface of the tooth and pulled over its surface toward the chewing edge.

It is known from surveys that most people, even including those who take seriously the matter of dental care and brushing regularly, do not use floss daily because the technique for use as described above is so tedious. For a number of years there have been attempts to render flossing less tedious and also to render it more effective by the development of holders onto which floss is attached. Most holders have two arms across which the floss is strung; however, secondary complications described below with the holders themselves have resulted in general non-use, and thus there has been no remedy to the original problem of promoting the regular use of floss held by hand.

One basic problem with the holders is that because they are non-disposable they are too large. Typical floss stretches on them, eventually frays and breaks during use. Whether the floss remains usable for five, twenty or more teeth depends upon the tightness of the interdental spaces and the abrasion the floss incurs. By the original manual flossing technique prior to using floss holders, the floss user merely pulled the exposed end of floss from a spool, cut off a segment and then wound the cut segment on the fingers. With certain floss holder devices the user must, for each flossing operation, obtain a length of floss, thread or carefully position it about a floss holder, pull on some part of the floss until it is in tension, and finally secure it under tension to the holder. Whether a floss supply is provided on a spool in the holder handle according to one device, or provided from a separate spool from which segments of floss are cut as needed, the remaining threading and tensioning procedure is still an inconvenient burden.

From these manually strung or manually loaded flossing devices there developed prestrung disposable flossers where a strand of floss of length to span the bow or spaced arms of the flosser had its ends secured to the arms in situ, namely at the same time the flosser handle and arms were injection molded. These devices have gained wide popularity and sales because they are convenient to use and to carry, and because they can be mass produced and sold at very low per unit cost.

Samples of prior art flossers of the type with an injection molded handle and floss prestrung at the time of molding, and disclosures of known manufacturing methods may be seen in U.S. Pat. Nos. 4,006,750, 4,016,892, 5,086,792, 5,538,023 and in the other patents cited above which are hereby incorporated herein by reference. These and similar devices, regardless of the geometric configuration of the handle, have certain useful features in common and certain troublesome features in common. These devices are light weight to use and inexpensive to manufacture, each with a bow portion formed by spaced arms and a segment of floss spanning the bow. Some configurations, as those with floss parallel to the handle, may be more convenient than others for particular users.

With some of these prior art disposable flossers having a permanently prestrung bow portion, the strand of floss becomes untaut due to stretching during use or the strand of floss was untaut due to the method of manufacture. Tensioning of the floss occurs each time the floss strand encounters resistance as it is urged to pass into the interspace between two closely or tightly adjacent teeth. After one or more uses of a strand of typical floss in a holder the floss will stretch and become slack, no longer being taut and linear between the arms or ends of the bow. Consequently, the next time the flosser with slack floss is used to penetrate the interspace between two teeth the floss takes a deep generally V-shaped configuration as penetration of the interspace is begun. This leads to two undesirable consequences. First, since the floss is not taut the bow must be moved further toward the gums than if the floss were taut. Secondly, the device becomes very difficult to use in a back and forth motion, especially when removing it.

Another reason why some prior art pre-strung flossers develop slack floss is because one or both floss ends slip slightly out of an arm of the bow during tensioning as the flosser is used. Slippage occurs when the floss is not well bonded to the holder which may occur because the plastics of the floss and handle are incompatible or because the floss and the injection molded plastic are not heated and cooled uniformly or at least not at appropriate respective temperatures and time periods for secure bonding to occur.

In conclusion, floss often stretches and subsequent attempts to use a flosser with stretched floss present difficulties or undesirable situations for the user. If the floss ends are well-anchored in the bow arms, stretching still occurs. If the floss ends are not well anchored the floss slips and slack results. Either way, after a few penetrations of interspaces many flossers have lost their tension of the floss.

For these pre-strung flossers a solution was developed to permit the user to create tautness or tension in the untaut strand by causing one or both arms of the bow to diverge from the other, this being achieved by the user squeezing appropriate parts of the dental floss holder between his/her thumb and one or more fingers. Flossers of the type which are designed to receive a fresh new strand of floss obviously can have each new strand applied tautly and thus do not incur the above-discussed stretching or looseness problem; however, new strands would have to be installed repeatedly.

In some tensioning flossers the users fingers must press one or more surfaces. Since economic factors lead to minimizing plastic and size, these flossers tend to be made of plastic having thin edges which cause pain when pressed. Alternative shapes, such as thickened edges or boxed three-dimensional shapes are more costly to make. U.S. Pat. No. 5,388,600 for example, while not a tensioning flosser has a three-dimensional boxed construction to provide a large gripping, surface, in addition to providing for stacking.

In the new invention I have identified problems and discovered solutions in the forms of a new device and a new method of manufacturing these devices, as set forth below.

SUMMARY OF THE INVENTION

The new invention is a disposable dental flossing holder which has some features of the prior art and certain new structure. From the prior art it has at least one strand of dental floss extending across arms of that is situated at the distal end of the handle. In the new device the handle has a central aperture situated between a pair of legs, where each leg continues in the distal direction to become one of the arms of the bow. The user can press and displace these two legs toward each other which will cause the corresponding arms of the bow to diverge slightly and thereby tighten or reduce slack in the strand of floss spanning the arm. In one alternative version there is only one displaceable leg to cause movement of a corresponding bow arm. In another alternative version the leg may be displaceable without any aperture, for example, merely by extending outward from the handle.

In any event relevant prior art tensioning flossers each typically has a handle that is a generally thin flat plank with opposite side edges which are thin. In a flosser of the type where the handle defines the one or more displaceable legs the user's thumb and finger are pressed against these thin edges which may be painful, causing the user to ease off and not apply the appropriate converging pressure.

In the new flosser the handle is similarly flat and defines a pair of legs which straddle the central aperture, but the thin side edges of the handle extend further outward as tabs or wings which are bendable to lie transversely and preferably at a 90° angle with respect to the basic handle.

The flosser including its handle as initially molded is a generally flat plank whose sides extend as wings or tabs. When the wings are bent downward they provide a pair of spaced apart parallel flat surfaces against which the user can press his/her thumb and forefinger in a totally comfortable operation as compared to the relevant prior art.

The method of manufacture in multi-cavity molds is known in the prior art, including in applicant's U.S. Pat. No. 4,006,750, which is hereby incorporated herein by reference. According to this method floss is positioned in a multi-cavity mold prior to injection molding of a suitable plastic into the cavities. The resulting product is complete and ready for use with no requirement of an additional step of threading, tensioning or securing floss; also it can be considerably less expensive than all other known holders which are designed to have the floss attached separately and furthermore tensioned.

Another feature of this invention is the intentional heating of the cut end of the floss to form a bead where the floss exits the arms, i.e. heating the floss either simultaneous with the cutting or as a separate step following cutting.

A further embodiment of this invention is a dental flosser with two or more lines of floss captured between the arms of the holder. This double or more lines of floss configuration is applicable to the tensioning flosser described above and to more traditional flossers having no tensioning capability. Advantages of this double line or "dual strand" flosser include increased cleaning action by the multiple strands of floss and providing back-up floss in case one strand frays or breaks. In some embodiments a finer denier would be used than in a typical single line flosser, which would facilitate passage between teeth.

A preferred embodiment comprises a flat holder having essentially uniform thickness, with a pair of wings or tabs extending outwardly from the handle where the user's fingers grasp or engage the holder. These wings are foldable to lie transversely or perpendicular to the handle; the users thumb and finger then press against the wide flat surface of the wing instead of against any thin edge. In another preferred embodiment the bow part of the flosser defines a plane at an angle from the plane of the handle.

In addition to designing a dental flosser for its use function, another consideration is the packaging of the product in multiples that will allow compact and attractive stacking. Without any thickened areas, a plurality of flossers can be stacked in a minimum space which reduces cost of packaging and allows more units to be displayed within a given space.

A still further aspect of dental flossing devices as applied to all the above-disclosed embodiments is the structural union of the injected molded plastic handle and the strand or strands of dental floss. Traditionally in the prior art the plastic materials for the handle and floss were selected to be chemically compatible to optimize the coupling or union of the floss within the arms of the flosser when the latter is injection molded with the floss in situ. However, selecting floss for its compatibility with the handle instead of for its flossing capabilities lead to flossers with inferior floss. On the other hand, failure to select chemically compatible plastics and floss led to floss not being secured to the handle and pulling out too easily. One approach to solve this problem is to have the floss extend out of the ends of the arms and to heat or burn these ends to coalesce into beads of diameter greater than the floss, which greatly resist being pulled through the channel in the arm through which the floss extends. This approach is not without its problems, in that some multifilamented floss material formed a single coalesced bead that did increase the diameter of the strand, but was not reliable to withstand the forces applied in flossing usage. Other floss materials or manufacturing methods for same resulted in blackening of the beaded ends when the floss was heated. Still other dental floss materials were difficult to cut during manufacture. Some plastics compatible with a floss were difficult to mold.

An aspect of the present invention is the combination of polypropylene for the injection molded plastic and the chemically incompatible twisted, multifilament ultra high molecular weight (UHMW) polyethylene for the floss, and finally, in the preferred embodiment to use a propane flame to cut and bead the floss where it extends out of the ends of the arms of the flossers. The propane flame cuts and coalesces the multifilament floss into a plurality of beads are on each filament, which are not blackened and which establish a spread or array having overall diameter substantially greater than the original floss diameter. The result is an excellent anchor to bar the floss from being pulled out of the arms during use. The polypropylene provides a superior crack-resistant, bendable which is relatively easy and inexpensive to mold. The twisted, multifilament polyethylene is extremely strong, optimally abrasive and highly lubricous, with a superior attachment to the arms as a result of the bead formation when this particular floss is heated in the required manner, preferably with a propane flame. Most important, the coefficient of elongation is only about three percent vs. more than twenty percent for Nylon.

The choice of polypropylene for the injection molded handle and twisted, multifilament UHMW polyethylene for the floss was not an obvious combination. Many different plastics have been tried for the injection molded handle and for the dental floss, each with disadvantages to be weighed against advantages. UHMW Polyethylene floss is not cut easily by knife or scissors and thus must be burned, which can cause carbonization and blackening. Heating and cutting multifilament Nylon, for example, produces less satisfactory beading at the ends. PTFE floss resists bonding.

It was determined that polypropylene, which molds well and has good strength, will securely hold dental floss of twisted, multifilament UHMW polyethylene when its ends are cut acid coalesced with a propane flame into an array of beads, each of which is very difficult to dislodge from the strand on which it is found. For all these flosser devices the new combination of materials for the handle and the dental floss, along with steps of manufacture produces a far superior product.

The embodiments of the invention summarized above will be described in greater detail below in conjunction with the drawings appended hereto.

DETAILED DESCRIPTION OF THE PREFERRED EMBODIMENTS

The dental flosser 10 of FIGS. 1–9 is a generally thin injection molded plastic sheet having a front end 12, a central handle part 14 and tail part 16. At the front end 12 is a bow 13 which comprises a pair of spaced apart arms 18*a*, 18*b* with a strand of dental floss 20 extending between and secured the tips 19 of the arms.

The central part 14 is formed by a pair of legs 22*a*, 22*b* spaced apart by an elongated generally oval aperture 24. Leg 22*a*, for example, is a continuation of arm 18*a*, and similarly leg 22*b* is a continuation of arm 18*b*.

Figure 6:
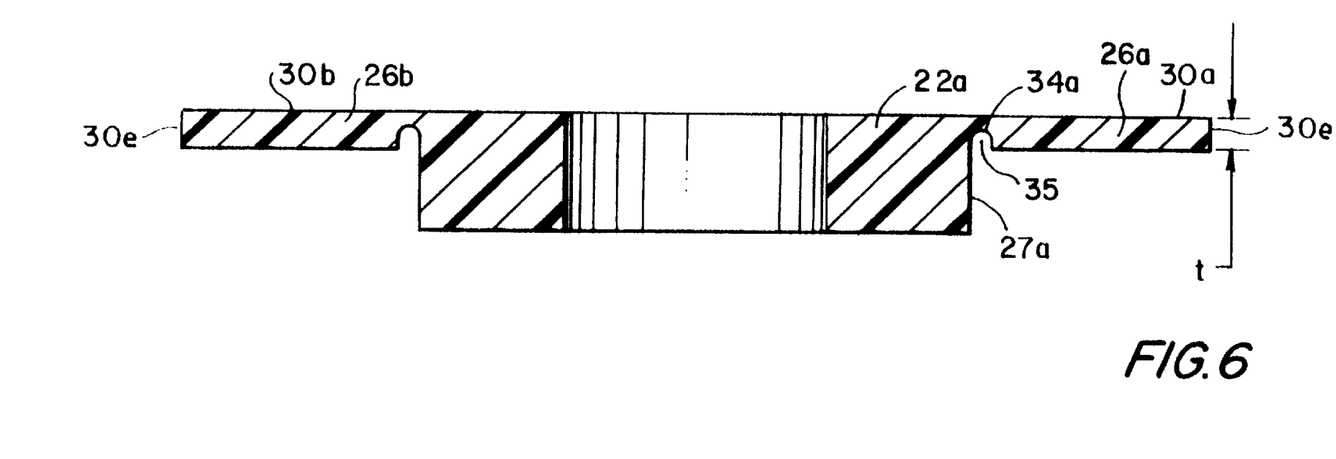
FIG. 6 is a sectional view taken along line 6—6 of FIG. 1.

Extending outward from legs 22*a*, 22*b* are wings 26*a*, 26*b* respectively, each with an outer edge 30*e* (as seen in FIG. 6).

Figure 4:
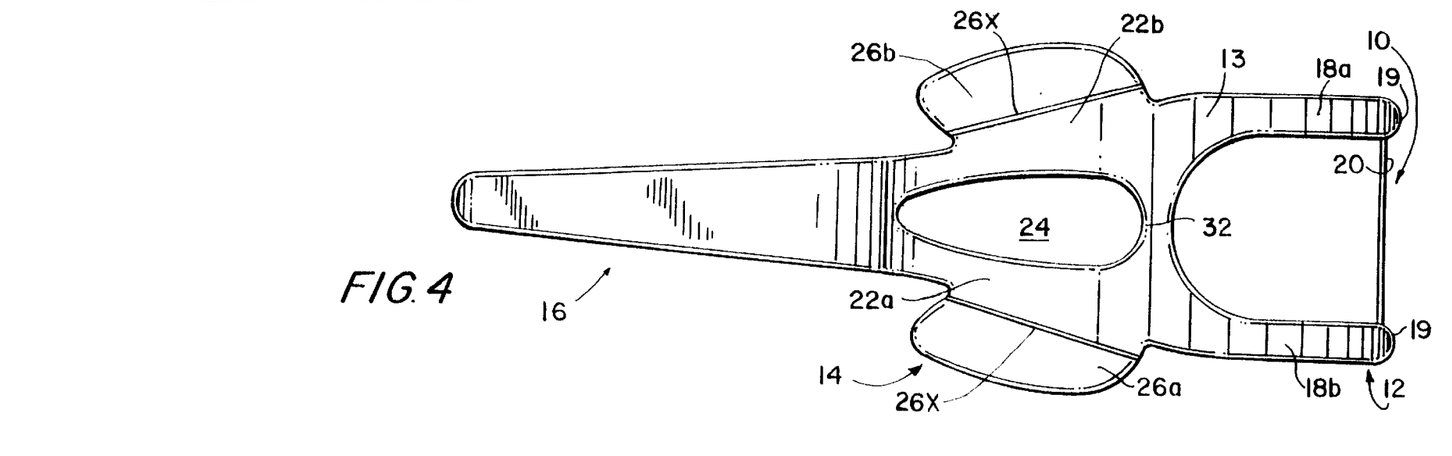
FIG. 4 is a bottom plan view thereof.
Figures 7, 9:
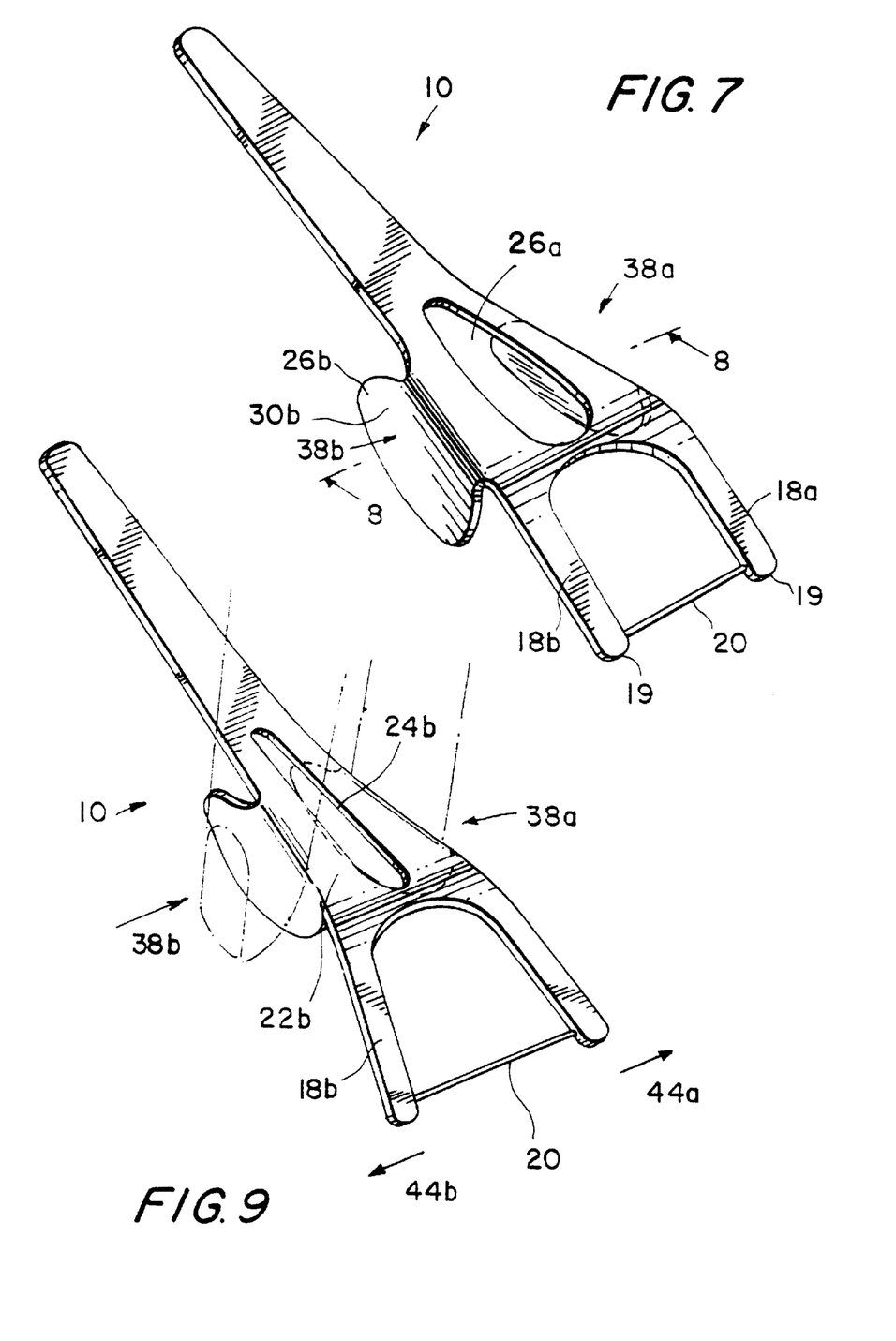
FIG. 7 is a top front perspective view similar to that of FIG. 1, but with wings bent downward.
FIG. 9 is a top front perspective view similar to FIG. 7 but with the handle squeezed to tension the dental floss.
Figure 8:
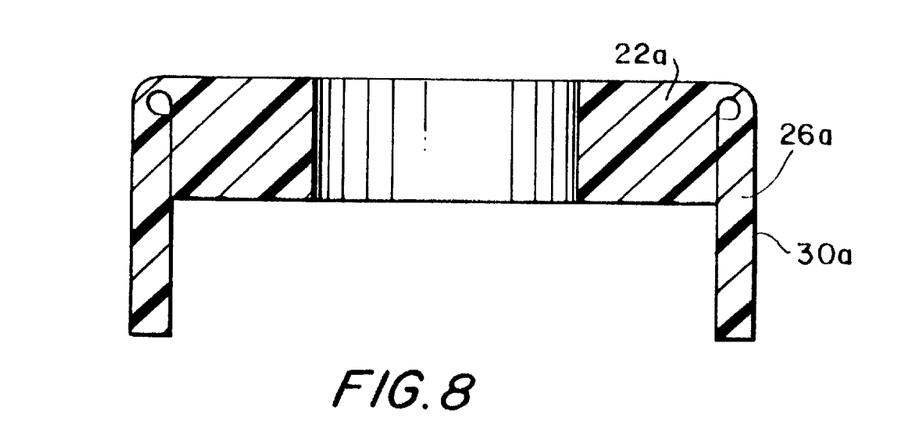
FIG. 8 is a sectional view taken along line 8—8 in FIG. 7, showing the wings bent.

Each wing is bendable downward as seen in FIGS. 7–9 to lie generally perpendicular to the plane of the handle. As seen in FIG. 6, the thickness t of the wing 26a is less than the thickness T of the handle 22a, so that as seen in FIG. 8, wing 26a folds only 90° and is stopped by edge 27a. Then wing 26b when bent for example, along bend line 26x in FIG. 4 presents a flat support surface 30a against which the user's finger or thumb is pressed. Wing 26b has a similar surface 30b when the wing is bent so it is easy and comfortable for a user to press surfaces 30a and 30b toward each other. Surfaces 30a and 30b as seen in FIG. 6 are top surfaces of wings 26a and 26b respectively which are generally co-planar with said handle before they are bent downward as seen in FIG. 8.

Because aperture 24 is substantially large, and neck 32 is relatively thin and weak, movement of legs 22a, 22b to converge causes arm extensions 18a and 18b respectively to diverge, thus tightening the strand of floss 20. The aperture may have variations in shape so long as at least one portion of the handle is displaceable to cause at least one arm of the bow to move outward from the other arm.

The tail part 16 at the rear left of the handle is helpful to stabilize the flosser when used, since the tail is engaged or surrounded by the palm and fingers for secure and/or leveraged engagement.

The flosser body, namely the bow 12, handle 14, tail 16 and wings are made of polypropylene which injection molds well, is strong and yet sufficiently flexible to function at the thin intersection or bend line 34a, 34b of each wing 26a, 26b and the adjacent central body parts (legs) 22a, 22b as a "living hinge" which is bendable a very great number of times without breaking.

The dental floss is preferably ultra high molecular weight polyethylene having the extremely desirable characteristics of adhering very well to the bow ends 19, and having great tensile strength and great resistance to stretching and fraying.

For a dental flosser to be commercially feasible and commercially successful it must be manufacturable in vast quantities for small unit cost. Also it has been discovered that these products must be packaged, displayed, presented and sold in compact attractive packages in quantities of about 20–60 to be commercially viable.

The new invention herein provides ultra high strength floss in a flosser with a floss tensioning feature that is easy and comfortable to use, all in a device that is injection molded in a generally flat state which is the least expensive to make, takes the least space when bundled or stacked in a package, and still is bendable to have the shape and advantages of a thick or three dimensional flosser.

Typical prior art flossers in U.S. Pat. No. 5,538,023 are either flat with a thin edge which may be painful to use on the user's fingers when the tensioning feature is used, or as seen in FIG. 7 of this reference the pressure edges 79 and 80 are thickened which adds cost of mold and molding. The new invention produces a wide flat pressure surface with a "thinner" wing that becomes folded.

This concept is even more dramatically seen when comparing the new invention to U.S. Pat. No. 5,388,600 which requires a deep cavity mold to produce a permanent side walls that make the device more expensive to make and occupy far more space in packaging of multiple units. This unit requires a more expensive multi-cavity mold, and ultimately occupies considerably more space in the package. Besides the manufacturing and packaging, the display space in stores allocated to products of this type is relatively small. One therefore needs to contain a maximum number of product units in the smallest space. This can be achieved when the basic unit begins as an essentially flat article which is stackable in minimum space and later used in a construction handle shape.

As seen in the figures, the preferred device shown is slightly bent in an undulating curve similarly as some forks. This is both attractive and functional while retaining the essentially flat shape with all the advantages and benefits discussed above.

This product can be made with materials and techniques knowing in the art as disclosed in the list of prior art patents included herein above particularly as regards selections of plastic, dental floss injection molding techniques, and methods of securing the ends of the floss in the ends of the arms of the bow.

In the preferred embodiment the total length is about 3¼ inches long, the strand of floss is about ⅝ inches long, and has denier of about 550; the handle is about 1/16 inches thick, As shown in FIGS. 7 and 9 the user can squeeze the flossing device shown herein by applying pressure surfaces 30a, 30b of the bent wings 26a, 26b, as indicated by arrows 38a, 38b. This causes aperture 24 in FIG. 7 to become narrowed to 24c as seen in FIG. 9, and for neck 32 to distort. Since arm 18b is an extension of leg 22b, movement of leg 32b inward toward its mating leg causes movement of arm 18b outward, as seen by diverging arrows 44a, 44b in FIG. 9 and consequent tensioning of floss strand 20.

Figure 1:
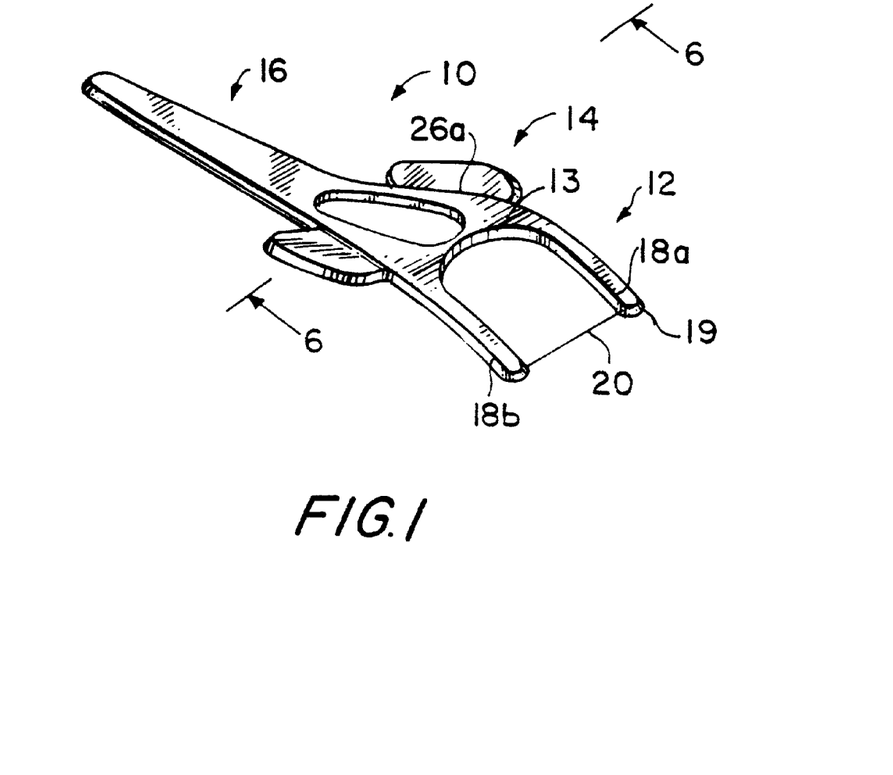
FIG. 1 is a top front perspective view of my new dental flosser.
Figure 2:
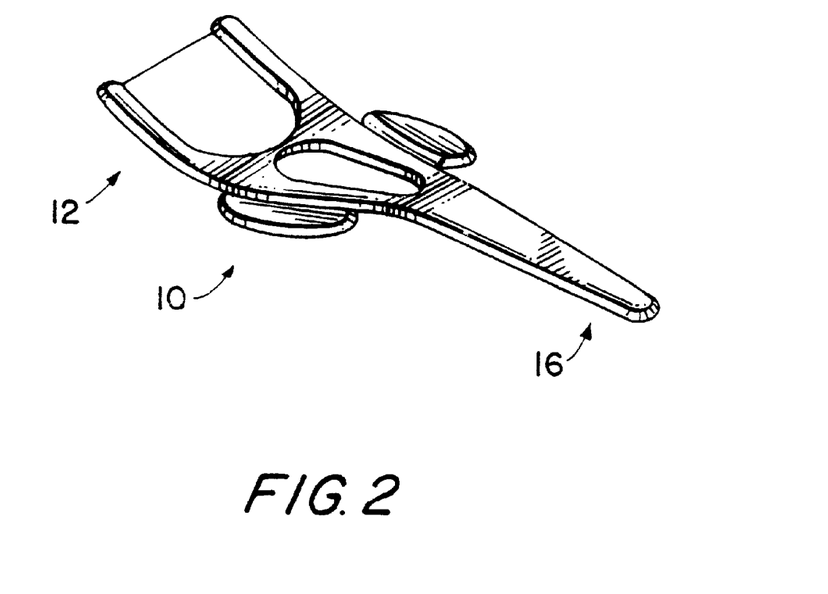
FIG. 2 is a bottom rear perspective view thereof.
Figures 3, 5:
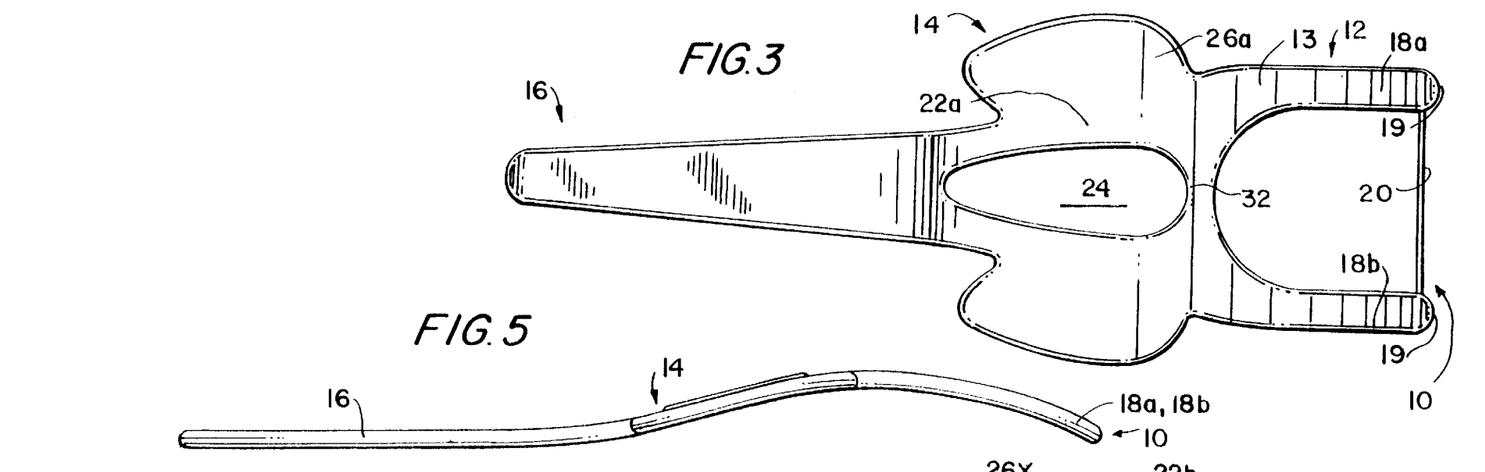
FIG. 3 is a top plan view thereof.
FIG. 5 is a right side elevation view thereof with a bow at the front and thereof.

In this preferred embodiment arms 18a, 18b are curved slightly as seen in FIG. 3 which allows easier access to interdental areas in some situations. Here the tail 16 is relatively straight, while the handle 14 and bow 12 define a smooth gentle curve.

Figure 13:
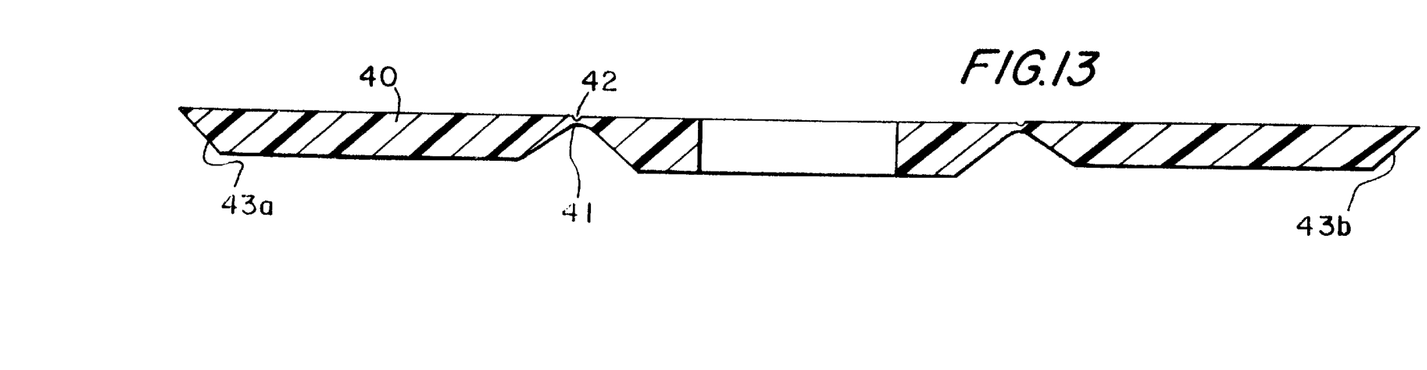
FIG. 13 is a schematic sectional view similar to FIG. 6 of a third embodiment of the new flosser.
Figure 14:
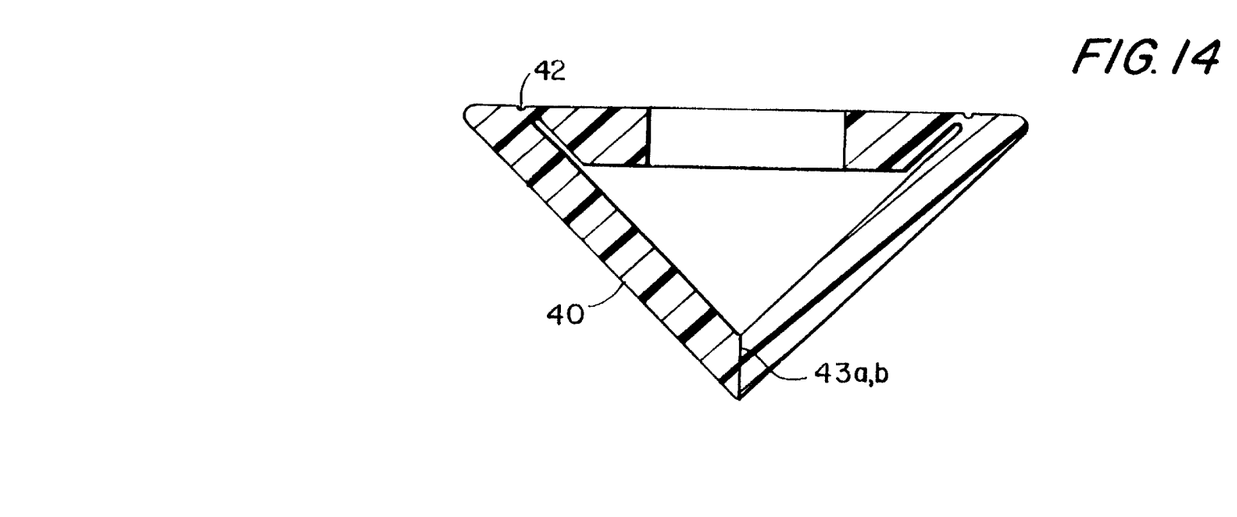
FIG. 14 is a sectional view similar to FIG. 8 of the embodiment of FIG. 13.

In FIGS. 6 and 8 the wings 26a, 26b are easily molded in the form seen with the small relief zone or reduced thickness 35 beneath the thin intersection 34a; however, a variety of other arrangements are possible for a bendable tab. For example, the tabs (wings) 40 could be of equal thickness to the handle as seen in FIGS. 13 and 14 with a V-shaped undercut 41 and a possible further recess 42 to allow a 135° bend to form a three dimensional handle of generally triangular section. Edges 43a, 43b may be coupled upon engagement by a variety of common coupling means not shown.

Figure 10:
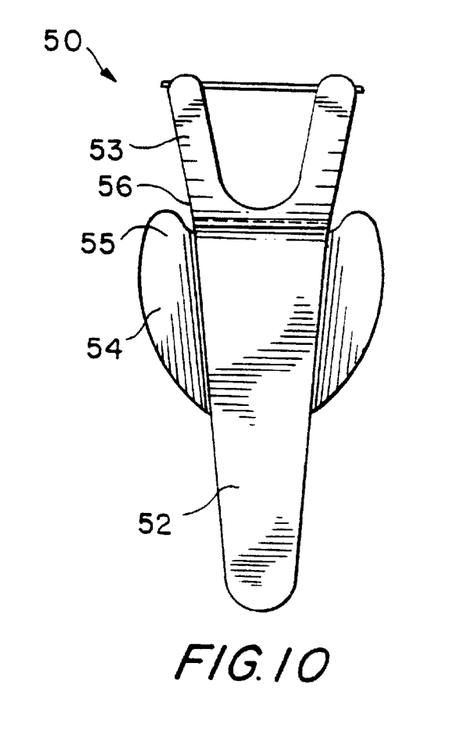
FIG. 10 is a top plan view of a second embodiment of the new flosser.
Figure 11:
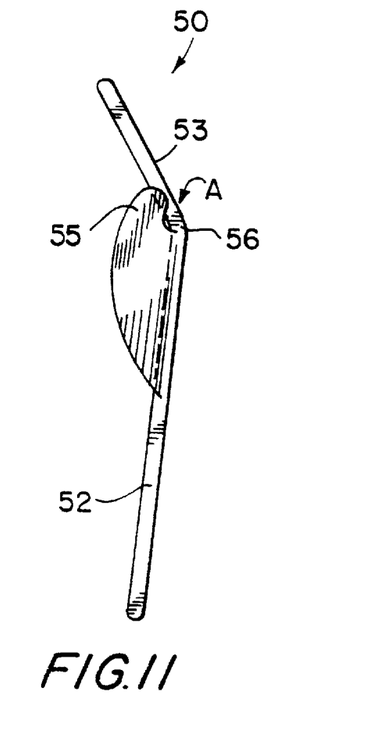
FIG. 11 is a left side elevation of FIG. 10.
Figure 12:
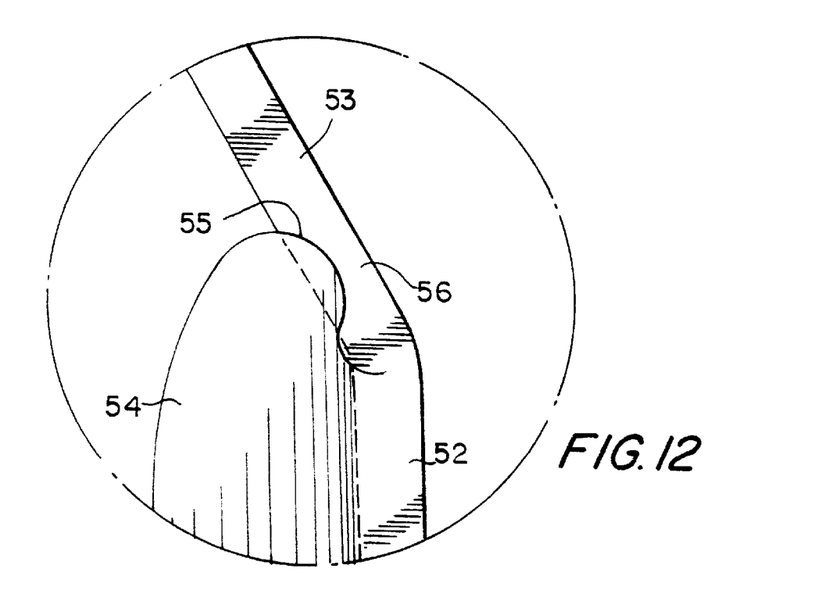
FIG. 12 is a fragmentary enlargement of area A in FIG. 11.

FIGS. 10–12 show an alternative structure for wings which can bend only 90°. The handle 52 defines a plane at an angle from the plane of the bow 53. Thus, when wing 54 bends downward 90° its distal end 55 engages edge 56 and is barred from bending further. FIG. 12 shows in enlarged fragmentary view of area A in FIG. 11 of the engagement of distal end 55 of wing 54 against edge 56 of the bow.

Figure 15:
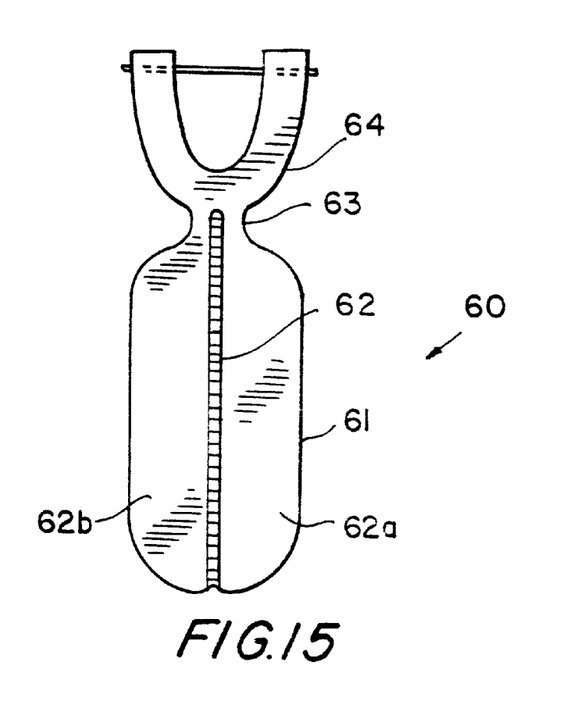
FIG. 15 is a top plan view of a fourth embodiment of the flosser.
Figure 16:
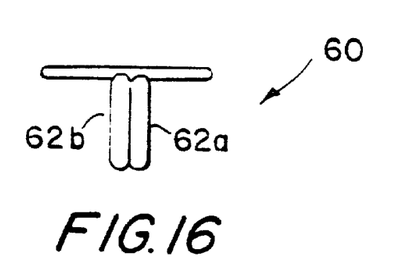
FIG. 16 is a rear end elevation view thereof.
Figure 17:
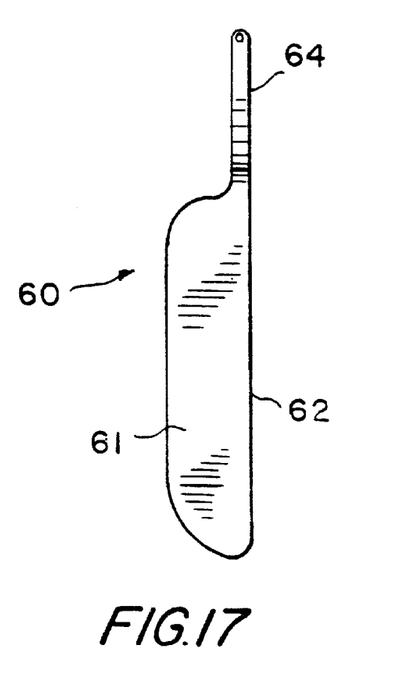
FIG. 17 is a left side elevation view thereof.
Figure 18:
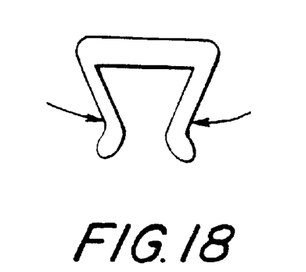
FIG. 18 is a sectional view similar to FIG. 8 of a still further embodiment.

A still further version of an initially flat handle which is bent to form a flat surface is seen in FIGS. 15–17 where flosser 60 has handle 61 and bend line 62. The handle has a pair of similar sides or wings 61b, 62b which fold to lie flat against each other as bow 64 remains transverse and in this case perpendicular to the bent handle. Relief cuts 65 allow the handle's wings to fold without interfering with the bow part 64.

The amount of bending of the handle wings may vary from 90° as seen in FIGS. 8 and 11, to 135° as seen in FIG. 14, to slightly more than 90°, all within the concept of laterally extending tabs or wings which bend to present a flat or less offensive engaging pressure surface than the essentially straight hard edge of prior art devices.

The above described embodiments of this invention may take a variety of other forms still within the spirit of this invention and within the scope of the claims appended hereto.

What is claimed is:

1. A dental flossing device comprising
a handle having proximal and distal parts,
a floss-engaging bow adjacent said distal parts formed of a pair of spaced-apart arms extending outward from said distal part and terminating in tip ends,
at least one strand of dental floss extending between and secured to said tip ends,
said handle and bow defining a generally elongated thin sheet, said distal part of said handle having opposite sides,
a wing extending outward from each of said opposite sides, each of said wings having top and bottom surfaces and a terminal edge, said top surface of each of said wings having greater area than said terminal edge thereof, each wing coupled to one of said sides by a hinge,
said handle, wings and hinges defining a plane,
said wings being bendable out of said plane to extend transversely of said plane.

2. A dental flossing device according to claim 1 wherein said handle's distal part comprises a pair of spaced-apart legs defining between them an aperture, each of said arms of said bow being a continuation of one of said legs, said legs being displaceable toward each other, thereby causing said arms to diverge from each other and thereby increasing tension in the strand of dental floss extending between said tip ends of said arms.

3. A device according to claim 2 where said bow defines a plane that is curved slightly downward relative to said plane of said handle.

4. A device according to claim 2 wherein said aperture is an elongated opening.

5. A device according to claim 2 wherein said aperture is an elongated oval opening extending through the full thickness of said distal part of said handle.

6. A device according to claim 2 further comprising stop means operable with said handle and said wings to bar said wings from bending more than 90° out of said plane of said handle.

7. A device according to claim 2 where each of said wings is bendable about 135° out of said plane of said handle and engages the other wing.

8. A device according to claim 1 wherein each of said hinges is a living hinge capable of a great plurality of bends without breaking.

9. A device according to claim 1 wherein each of said wings defines a tab having length and breadth and having thickness no greater than that of said handle's distal part.

10. A device according to claim 9 wherein each of said wings has thickness less than that of said handle's distal part.

11. A device according to claim 10 wherein said distal part has top and bottom surfaces, and each of said wings has a top surface that is coplanar with said top surface of said distal part.

12. A device according to claim 9 wherein each of said wings has length in the range of ¼ inch to 1½ inches and breadth in the range of ⅛ to ½ inch.

13. A device according to claim 9 wherein said handle and bow have thickness of about 1/16 inch and said wings have thickness of about 3/64 inch.

14. A device according to claim 1 wherein said handle, wings, bow and hinges comprise a single contiguous injection molded plastic sheet.

15. A device according to claim 1 wherein said aperture is an elongated oval opening extending through the full thickness of said distal part of said handle.

16. A device according to claim 1 further comprising stop means operable with said handle and said wings to bar said wings from bending more than 90° out of said plane of said handle.

17. A device according to claim 1 where each of said wings is bendable about 135° out of said plane of said handle and engages the other wing.

18. A dental flossing device comprising
a handle having proximal and distal parts,
a floss-engaging bow adjacent said distal part formed of a pair of spaced-apart arms extending outward from said distal part and terminating in tip ends,
at least one strand of dental floss extending between and secured to said tip ends,
said handle and bow defining a generally elongated thin sheet, said distal part of said handle having opposite sides,
a wing extending outward from at least one of said opposite sides, said at least one wing coupled to one of said sides by a hinge and having a terminal edge,
said handle, at least one wing and hinge defining a plane,
said at least one wing being bendable out of said plane to extend transversely of said plane to provide a surface having greater area than the area of said terminal edge of said wing.

19. A dental flossing device comprising
a handle having proximal and distal parts,
a floss-engaging bow adjacent said distal part formed of a pair of spaced-apart arms extending outward from said distal part and terminating in tip ends,
at least one strand of dental floss extending between and secured to said tip ends,
said handle and bow defining a generally elongated thin sheet, said distal part of said handle having opposite sides,
a wing extending outward from each of said sides, with a bend line defined between each of said wings and said side from which it extends, said handle defining a plane,
said wings being bendable along said bend lines out of said plane to extend generally perpendicularly to said plane.

20. A dental flossing device according to claim 19, wherein said handle's distal part comprises a pair of spaced-apart legs defining between them an aperture, each of said arms of said bow being a continuation of one of said legs, said legs being displaceable toward each other thereby causing said arms to diverge from each other and thereby increasing tension in the strand of dental floss extending between said tip ends of said arms.

21. A dental flossing device comprising
a handle having proximal and distal parts,
a floss-engaging bow adjacent said distal part formed of a pair of spaced-apart arms extending outward from said distal part and terminating in tip ends,
at least one strand of dental floss extending between and secured to said tip ends,
said handle and bow defining a generally elongated thin sheet, said distal part of said handle having opposite sides,
a wing extending outward from each of said sides, each wing defining at the intersection of said wing and the side from which it extends a bend line,
said handle and said wings defining a plane, each of said wings being bendable along said bend line corresponding thereto out of said plane to extend transversely of said plane.

22. A dental flossing device according to claim 21, wherein said handle's distal part comprises a pair of spaced-apart legs defining between them an aperture, each of said arms of said bow being a continuation of one of said legs, said legs being displaceable toward each other, thereby causing said arms to diverge from each other and thereby increasing tension in the strand of dental floss extending between said tip ends of said arms.

23. A dental flossing device according to claim 21 wherein each of said intersections between a side of said handle and one of said wings has thickness less than that of said side and said wing.

* * * * *